United States Patent

Cazaux et al.

Patent Number: 6,107,495
Date of Patent: Aug. 22, 2000

[54] THIENYLCYCLOHEXANE DERIVATIVES FOR THIENYLCYCLOHEXYL SYNTHESIS

[75] Inventors: Jean-Bernard Cazaux, Aramon; Michel Dafniet, Villeneuve les Avignon; Jean-Marc Kamenka; Eric Manginot, both of Montpellier, all of France

[73] Assignee: Societe d'Expansion Scientifique Expansia, France

[21] Appl. No.: 09/230,237

[22] PCT Filed: Jul. 24, 1997

[86] PCT No.: PCT/FR97/01382

§ 371 Date: Jan. 19, 1999

§ 102(e) Date: Jan. 19, 1999

[87] PCT Pub. No.: WO98/03498

PCT Pub. Date: Jan. 29, 1998

[30] Foreign Application Priority Data

Jul. 24, 1996 [FR] France .................... 96 09277

[51] Int. Cl.$^7$ .................. C07D 333/12; C07D 333/22; C07D 333/24
[52] U.S. Cl. .................. 549/74; 549/76; 549/79
[58] Field of Search .................. 549/74, 76, 79

[56] References Cited

U.S. PATENT DOCUMENTS 4,138,137  2/1979  Pigerol et al. .

FOREIGN PATENT DOCUMENTS 2271225  12/1974  France .
2272660  12/1975  France .
2421897  11/1979  France .

OTHER PUBLICATIONS

Michaud et al, "Homochiral . . . Receptor Sites", European Journal of Medicinal Chemistrychimica Therapeutica, vol. 29, No. 11, 1994 Paris, France, pp. 869–876.

Ouyang et al, Syntheses . . . Calcium Ionophore, Chemical Abstracts, & Nucl. Med. Biol. vol. 125, No. 5, Jul. 29, 1996, Abstract No. 52501.

Vol. 23, No. 3, 1996, pp. 315–324.

Mousseron et al, "Syntheses . . . La Phencyclidine", Chimica Therapeutica, vol. 3, No. 4, 1968, Paris, France, pp. 241–247.

Kalir et al, "1–Phenylcycloalkylamine Derivatives. III", Chemical Abstracts, vol. 85, No. 3, Jul. 19, 1976, Abstract No. 13673 & Isr. J. Chem., vol. 13, No. 2, 1975, Israel, pp. 125–136.

Primary Examiner—Deborah C. Lambkin
Attorney, Agent, or Firm—Bierman, Muserlian and Lucas

[57] ABSTRACT

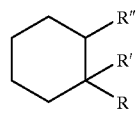

(I)

Novel thienylcyclohexane derivatives of general formula (I), wherein R' is the 2-thienyl or 3-thienyl radical, R is the cyano radical or a radical of formula —C(O)A, and R2" is a saturated or unsaturated optionally cyclic hydrocarbon radical, or an aryl radical, are disclosed. Methods for preparing said compounds, and the use thereof as novel industrial products for the synthesis of thienylcyclohexyl derivatives, are also disclosed.

8 Claims, No Drawings

THIENYLCYCLOHEXANE DERIVATIVES FOR THIENYLCYCLOHEXYL SYNTHESIS

This application is a 371 of PCT/FR97/01382 filed Jul. 24, 1997.

The present invention relates to new thienylcyclohexane derivatives, processes for their preparation and their use as new industrial products for the synthesis of thienylcyclohexyl derivatives, and more particularly cyclic (thienylcyclohexyl) amines.

A subject of the invention is the compounds of general formula I

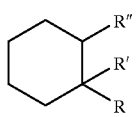

I in racemic form, or in the form of substantially pure diastereoisomers or enantiomers, in which R represents the cyano radical;

a radical of formula —C(O)A in which A represents a halogen atom; a radical of formula $OR_1$ or $NR_2R_3$ in which $R_1$, $R_2$ and $R_3$ represent, independently, a hydrogen atom or an alkyl, alkenyl or alkynyl group, the alkyl, alkenyl and alkynyl radicals being optionally substituted by one or more identical or different substituents chosen from halogen atoms; the substituents hydroxy; alkoxy; alkylthio; acyl; free, salified or esterified carboxy; cyano; nitro; amino optionally substituted by one or more identical or different alkyl radicals; or cycloalkyl or aryl, the cycloalkyl and aryl radicals being optionally substituted by one or more identical or different radicals chosen from halogen atoms, the hydroxy, alkyl, alkenyl, haloalkyl, alkoxy, alkylthio, acyl, free, salified or esterified carboxy, cyano, nitro or amino radicals optionally substituted by one or more identical or different alkyl radicals;

a radical of formula —$NR_4R_5$ in which $R_4$ and $R_5$ represent, independently, a hydrogen atom or an alkyl, alkenyl or alkynyl radical, the alkyl, alkenyl and alkynyl radicals being optionally substituted by one or more identical or different radicals, chosen from halogen atoms; the substituents hydroxy; alkoxy; alkylthio; acyl; free, salified or esterified carboxy; cyano; nitro; amino optionally substituted by one or more identical or different alkyl radicals; or cycloalkyl or aryl, the cycloalkyl and aryl radicals being optionally substituted by one or more identical or different radicals, chosen from halogen atoms, the substituents hydroxy, alkyl, alkenyl, haloalkyl, alkoxy, alkylthio, acyl, free, salified or esterified carboxy, cyano, nitro or amino optionally substituted by one or more identical or different alkyl radicals;

R' represents the 2-thienyl or 3-thienyl radical;

R" represents an alkyl, alkenyl or alkynyl radical, these alkyl, alkenyl and alkynyl radicals being optionally substituted by one or more identical or different radicals, chosen from halogen atoms; the substituents hydroxy; alkoxy; alkylthio; acyl; free, salified or esterified carboxy; cyano; nitro; amino optionally substituted by one or more identical or different alkyl radicals; or cycloalkyl or aryl, the cycloalkyl and aryl radicals being optionally substituted by one or more identical or different radicals, chosen from halogen atoms, the substituents hydroxy, alkyl, alkenyl, acyl, free, salified or esterified carboxy, alkoxy, alkylthio, acyl, free, salified or esterified carboxy, cyano, nitro or amino optionally substituted by one or more identical or different alkyl radicals;

a cycloalkyl or cycloalkenyl radical, the cycloalkyl and cycloalkenyl radicals being optionally substituted by one or more identical or different substituents, chosen from halogen atoms, the substituents hydroxy, alkyl, alkenyl, haloalkyl, alkoxy, alkylthio, acyl, free, salified or esterified carboxy, cyano, nitro or amino optionally substituted by one or more identical or different alkyl radicals;

an aryl radical optionally substituted by one or more identical or different substituents, chosen from halogen atoms, the substituents hydroxy, alkyl, alkenyl, haloalkyl, alkoxy, alkylthio, acyl, free, salified or esterified carboxy, cyano, nitro or amino optionally substituted by one or more identical or different alkyl radicals;

as well as the salts of these compounds with mineral or organic acids, excluding the compound, in racemic form, in which R represents the amino radical, R' represents the 2-thienyl radical and R" represents the methyl radical.

In the expressions indicated above, the expression halogen represents a fluroine, chlorine, bromine or iodine atom, preferably chlorine.

The term alkyl designates a linear or branched alkyl radical comprising 1 to 12 carbon atoms. Preferably, the term alkyl represents a linear or branched alkyl radical having 1 to 6 carbon atoms, and in particular the methyl, ethyl, propyl, isopropyl, butyl, isobutyl, sec-butyl and tert-butyl, pentyl, isopentyl, hexyl, isohexyl radicals.

The term alkenyl designates a linear or branched alkenyl radical comprising 1 to 12 carbon atoms. Preferably, the term alkenyl represents a linear or branched alkenyl radical having 1 to 6 carbon atoms, and in particular the vinyl, allyl, propenyl, butenyl, pentenyl or hexenyl radicals.

The term alkynyl designates an alkynyl radical, linear or branched, comprising 1 to 12 carbon atoms. Preferably, the term alkynyl represents a linear or branched alkynyl radical having 1 to 6 carbon atoms, and in particular the ethynyl, propynyl, butynyl, pentynyl or hexynyl radicals.

The term alkylthio designates the radicals in which the alkyl radical has the meaning indicated above. Preferably, the term alkylthio represents a methylthio, ethylthio, propylthio, butylthio or pentylthio radical.

The term haloalkyl preferably designates the radicals in which the alkyl radical has the meaning indicated above, substituted by one or more halogen atoms as defined above. The term haloalkyl can represent for example a trifluoromethyl, trifluoroethyl or bromoethyl radical.

The alkoxy radicals designate the radicals of which the alkyl radical has the meaning indicated above. The methoxy, ethoxy, isopropyloxy or tert-butyloxy radicals are preferred.

The expression cycloalkyl or cycloalkenyl designates a saturated or unsaturated, hydrocarbonated cycle, with 3 to 7 carbon atoms. The saturated cycloalkyl radicals can be chosen from the cyclopropyl, cyclobutyl, cyclopentyl, cyclohexyl or cycloheptyl radicals. The unsaturated cycloalkyl radicals can be chosen from the cyclobutenyl, cyclopentenyl, cyclohexenyl, cyclopentadienyl, cyclohexadienyl radicals.

The expression amino optionally substituted by one or more identical or different alkyl radicals, represents the amino radical optionally substituted by one or more alkyl radicals as defined above. Preferably, this expression designates the amino radical, the monoalkylamino radicals such as methylamino or ethylamino, or dialkylamino such as dimethylamino or diethylamino.

The expression acyl designates an acyl radical having from 1 to 6 carbon atoms such as, for example, the formyl, acetyl, propionyl, butyryl, pentanoyl, hexanoyl, acryloyl, crotonoyl or benzoyl radical.

The expression aryl represents an aromatic radical, constituted by a cycle or condensed cycles; each cycle can optionally contain one or more identical or different heteroatoms, chosen from sulphur, nitrogen or oxygen. Examples of an aryl radical are the phenyl, naphthyl, thienyl, furyl, pyrrolyl, imidazolyl, pyrazolyl, isothiazolyl, thiazolyl, isoxazolyl, oxazolyl, pyridyl, pyrazinyl, pyrimidyl, benzothienyl, benzofuryl and indolyl radicals.

A more particular subject of the invention is the compounds of general formula I as defined above, in which R represents the cyano radical;
a radical of formula —C(O)A in which A represents a chlorine atom;
a radical of formula $OR_1$ or $NR_2R_3$,
in which $R_1$, $R_2$ and $R_3$ represent, independently, a hydrogen atom, an alkyl, alkenyl or alkynyl radical,
the alkyl, alkenyl and alkynyl radicals containing from 1 to 6 carbon atoms and optionally substituted by one or more identical or different radicals, chosen from the fluorine, chlorine, bromine or iodine atoms, hydroxy, methoxy, ethoxy, isopropyloxy, ter-butyloxy, methylthio, ethylthio, propylthio, butylthio, pentylthio, acyl, carboxy, cyano, nitro, optionally substituted amino, cyclopropyl, cyclobutyl, cyclopentyl, cyclohexyl, cycloheptyl or phenyl groups, the cyclopropyl, cyclobutyl, cyclopentyl, cyclohexyl, cycloheptyl and phenyl radicals being optionally substituted;
a radical of formula —$NR_4R_5$ in which $R_4$ and $R_5$ represent, independently, a hydrogen atom, an alkyl, alkenyl or alkynyl radical,
the alkyl, alkenyl and alkynyl radicals containing from 1 to 6 carbon atoms and optionally substituted by one or more identical or different radicals, chosen from fluorine, chlorine, bromine or iodine atoms, hydroxy, methoxy, ethoxy, isopropyloxy, ter-butyloxy, methylthio, ethylthio, propylthio, butylthio, pentylthio, acyl, carboxy, cyano, nitro, optionally substituted amino, cyclopropyl, cyclobutyl, cyclopentyl, cyclohexyl, cycloheptyl, phenyl groups, the cyclopropyl, cyclobutyl, cyclopentyl, cyclohexyl, cycloheptyl and phenyl radicals being optionally substituted;

R' represents the 2-thienyl or 3-thienyl radical;
R" represents an alkyl, alkenyl or alkynyl radical,
the alkyl, alkenyl and alkynyl radicals containing from 1 to 6 carbon atoms and optionally substituted by one or more identical or different radicals, chosen from the fluorine, chlorine, bromine or iodine atoms, the hydroxy, methoxy, ethoxy, isopropyloxy, ter-butyloxy, methylthio, ethylthio, propylthio, butylthio, pentylthio, acyl, carboxy, cyano, nitro, optionally substituted amino, cyclopropyl, cyclobutyl, cyclopentyl, cyclohexyl, cycloheptyl, phenyl groups, the cyclopropyl, cyclobutyl, cyclopentyl, cyclohexyl, cycloheptyl and phenyl radicals being optionally substituted;

a cyclopropyl, cyclobutyl, cyclopentyl, cyclohexyl or cycloheptyl radical, these radicals being optionally substituted by one or more identical or different radicals, chosen from fluorine, chlorine, bromine or iodine atoms, hydroxy, methoxy, ethoxy, isopropyloxy, ter-butyloxy, methylthio, ethylthio, propylthio, butylthio, pentylthio, acyl, carboxy, cyano, nitro or amino radicals, optionally substituted;

a phenyl, naphthyl, thienyl, furyl, pyrrolyl, imidazolyl, pyrazolyl, isothiazole, thiazole, isoxazolyl, oxazolyl, pyridyl, pyrazyl, pyrimidyl, benzothienyl, benzofuryl or indolyl radical, these radicals being optionally substituted by one or more identical or different radicals, chosen from fluorine, chlorine, bromine or iodine atoms, hydroxy, methoxy, ethoxy, isopropyloxy, ter-butyloxy, methylthio, ethylthio, propylthio, butylthio, pentylthio, acyl, carboxy, cyano, nitro or amino radicals, optionally substituted; as well as the salts of these products.

A more particular subject of the invention is the products described below in the examples, in particular the products corresponding to the following formulae:

2-methyl-1-(2-thienyl)cyclohexane carbonitrile;
2-methyl-1-(2-thienyl)cyclohexane carboxylic acid;
ethyl 2-methyl-1-(2-thienyl)cyclohexane carboxylate;
2-methyl-1-(2-thienyl)cyclohexane carboxamide;
N-[α-methyl-((S)-phenylmethyl)]2-methyl-1-(2-thienyl) cyclohexane carboxamide;
2-methyl-1-(3-thienyl)cyclohexane carbonitrile;
2-methyl-1-(3-thienyl)cyclohexane carboxylic acid;
2-methyl-1-(3-thienyl)cyclohexane carboxamide;
2-methyl-1-(3-thienyl)cyclohexylamine;
2-ethyl-1-(2-thienyl)cyclohexane carbonitrile;
2-propyl-1-(2-thienyl)cyclohexane carbonitrile;
2-benzyl-1-(2-thienyl)cyclohexane carbonitrile
2-phenyl-1-(2-thienyl)cyclohexane carbonitrile
in racemic form or in the form of substantially pure diastereoisomers or enantiomers.

A subject of the invention is also a process for the preparation of compounds of general formula I as defined above in which R represents the cyano radical or a radical of formula —C(O)A in which A represents a radical of formula $OR_1$ or $N_2R_3$ as defined above, characterized in that a product of general formula 1

$$R'CH_2R \qquad\qquad 1$$

in which R and R' have the meanings indicated above, is reacted with a product of general formula 2

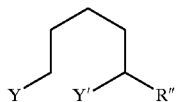

in which Y and Y' represent, independently, parting groups and R" has the meaning indicated above, in an inert solvent, in the presence of a strong base, in order to produce a product of formula I.

The use of starting compounds in racemic form enables compounds of formula I to be obtained in racemic form. The use of a compound of formula 2, in (R) or (S) form, allows a compound of formula I to be obtained in the form of a substantially pure enantiomer.

In the product of formula 2, Y and Y' represent parting groups such as a halogen, and preferably a chlorine atom, or an aryl or alkylsulphonate radical.

For the implementation of the process above, an inert solvent is used for the reaction such as, for example, acetonitrile, dimethylacetamide or dimethylformamide, and preferably dimethylformamide, in the presence of a strong base. The strong base can be chosen from products such as an alkyllithium (such as for example a methyl-, n-butyl- or t-butyl-lithium) or one of its derivatives such as, for example, lithium diisopropylamide (LDA) or lithium hexamethyldisilazane (LiHMDS), an alkaline alcoholate (for example a methylate, ethylate, propylate, butylate, tert-butylate, isoamylate or tert-amylate) or an alkali metal hydroxide. The compound of formula 1 is then added to said solvent, in the presence of a strong base, at a temperature comprised between −80° C. and ambient temperature, preferably between −20° C. and 0° C. The compound of formula 2 is then added at a temperature comprised between −10° C. and +10° C., preferably at a temperature slightly below 0° C. The reaction medium is then heated to a temperature comprised between 20 and 65° C. and maintained under agitation for 15 minutes to several hours. The reaction can be followed for example by chromatography (thin layer, gas or liquid as appropriate). Once the reaction is complete, the solvent is partially eliminated under reduced pressure and the residue treated with a mixture of water and solvent which is non-miscible with water in order to extract the reaction product.

The products of general formula 1 are commercially available or can be obtained by standard methods known to a person skilled in the art.

The products of general formula 2 can be obtained, for example, either by the reaction of an organometallic compound on valerolactone, or one of its derivatives, followed by reduction then by the appropriate substitution of the hydroxy groups, or by reaction of an organometallic of formula R″—M-Hal on an alkyl 4-(halogenoformyl) butyrate followed by reduction then by the appropriate substitution of the hydroxy groups, or also by reaction of an organometallic of formula R″—M-Hal on the appropriate compound of general formula Y—(CH$_2$)$_4$—C(O)Hal followed by reduction then by the appropriate substitution of the hydroxy group, according to reaction diagram 1 below. The organometallic compound as defined above can be an organomagnesium compound or a compound obtained by exchange between an organomagnesium compound and a metallic halide such as, for example, copper or manganese chloride, or another product known to a person skilled in the art.

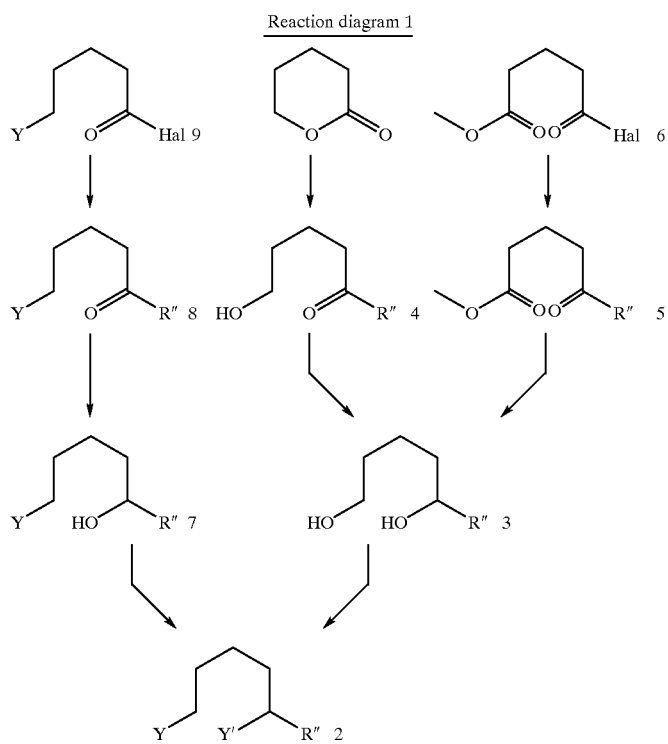

Reaction diagram 1

The compounds of formula 2 can also be obtained according to reaction diagram 2 below, by reduction of the ketone of formula R″C(O)(CH$_2$)$_2$CH=CH in which R″ has the meaning indicated above, then the appropriate substitution of the hydroxy group formed in this way, followed by the conversion of the alkene into the corresponding alcohol and finally the appropriate substitution of the hydroxy group formed in this way.

The compounds of formula 2 in the form of a substantially pure enantiomer can be prepared according to reaction diagram 2, for example, by incorporating an additional step for separating the alcohols of formula R″C(OH)(CH$_2$)$_2$CH=CH in the form of a substantially pure enantiomer, then the treatment of one of the alcohols for the formation of the corresponding compound 2, in the desired substantially pure form. In the case where the separation of the alcohols in substantially pure form is difficult, the alcohol in racemic form can be converted into another compound the enantiomeric forms of which are more easy to separate; for example, the alcohol can be reacted with phthalic anhydride, then the diastereoisomeric forms can be separated from the phthalate formed in this way, and the phthalate, in the form of a substantially pure diastereoisomer, can be converted into the corresponding alcohol, in the form of a substantially pure enantiomer, and finally the alcohol can be treated according to reaction diagram 2.

Reaction diagram 2

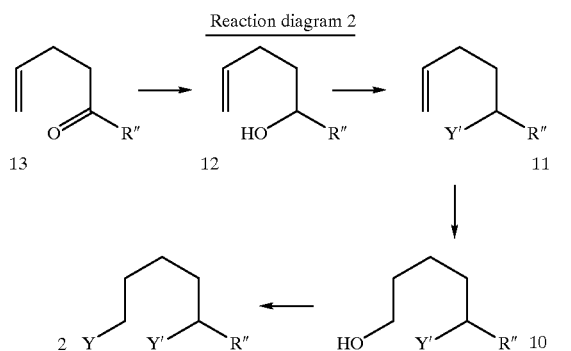

In these reaction diagrams 1 and 2, Y, Y' and R" have the meaning indicated above and Hal represents a halogen atom.

The compounds of general formula I as defined above, in which R represents the —NR$_4$R$_5$ radical, can be obtained starting from the corresponding compound of formula 1 in which R represents the —C(O)NR$_2$R$_3$ radical under standard operating conditions known to a person skilled in the art.

The compounds of general formula I as defined above in which R represents an acid, amide or ester function can also be obtained directly or indirectly starting from the corresponding compound of formula I in which R represents the cyano radical, under standard operating conditions known to a person skilled in the art, according to the following reaction diagram 3.

Reaction diagram 3

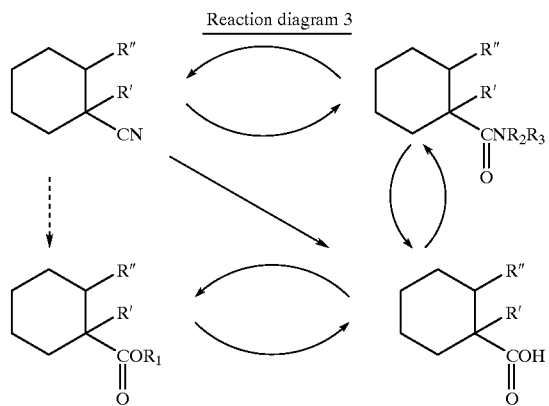

The compounds which are a subject of the invention can therefore be obtained in racemic form starting from starting compounds in racemic form. They can also be obtained with a predominant cis or trans configuration between the R and R" groups. The use of a compound of formula 2, in (R) or (S) form, allows a single enantiomer to be obtained along the full length of the synthetic chain. Moreover, at each stage of the the chain formation, chemical or enzymatic resolution is possible.

Enzymatic resolution at the stage of the compound of formula I, in which R represents the nitrile, amide or ester function, is possible with, for example, a nitrilase, a hydratase or acylase amide, or an esterase respectively. In the case of the ester, Pig Liver Esterase is preferably used.

The chemical resolution can be carried out with a chiral amine at the stage of the compound of formula I in which R represents the acid function. The amine can be chosen from the chiral amines known to a person skilled in the art. Preferably, quinine or α-methyl-benzylamine is used. In the case of resolution with quinine, the salt of the (+) acid crystallizes preferentially. Obtaining the (−) acid can be achieved by precipitation of its salt with D-(+) α-methyl-benzylamine. Similarly, resolution can be carried out at the stage of the compound of formula I in which R represents an amine function by using optically active acids, and preferably tartaric acid or a derivative of tartaric acid such as di-O,O'-toluoyltartaric.

The compounds of general formula I in which R represents the amino radical, are precursors of the compounds of formula II

in which R' and R" have the meanings indicated above and E$_1$ and E$_2$ are linked together and together with the nitrogen atom to which they are attached form a heterocycloalkyl or heterocycloalkenyl. The expression heterocycloalkyl or heterocycloalkenyl designates a cycloalkyl, saturated or unsaturated, containing from 3 to 5 carbon atoms and at least one heteroatom. This radical can contain several identical or different heteroatoms. Preferably, the heteroatoms are chosen from oxygen, sulphur or nitrogen. Examples of heterocycloalkyl or heterocycloalkenyl radicals are the pyrrolidinyl, imidazolidinyl, pyrrazolidinyl, piperidyl, piperazinyl, morpholinyl, isothiazolidyl, thiazolidyl, isoxazolidyl, oxazolidyl and 1,2,3,6-tetrahydropyridyl radicals.

Thus the compounds of general formula II can be obtained by reacting on the corresponding compound of formula I in which R represents the amino radical, a compound of formula Hal-B-Hal in which Hal represents a halogen atom and B represents an appropriate hydrocarbonated chain with 3 to 8 carbon atoms, which is saturated or unsaturated, under standard operating conditions known to a person skilled in the art. The compounds of general formula Hal-B-Hal are commercial or can be obtained by standard methods known to a person skilled in the art starting from the corresponding diol of formula HO—B—OH.

A subject of the invention is therefore also the use of compounds of general formula I as defined above, as new industrial products for the synthesis of thienylcyclohexyl derivatives, and more particularly cyclic (thienylcyclohexy) lamines. A more particular subject of the invention is the use of compounds of general formula I as defined above in which R" represents an alkyl radical, for the synthesis of 2-alkyl-(3-thienyl)cyclohexyl piperidine or 2-alkyl-(2-thienyl)cyclohexyl piperidine, in racemic form, in the form of a substantially pure diastereoisomer or enantiomer. A more particular subject of the invention is the use of 2-methyl-1-(2-thienyl)cyclohexylamine in the form of a substantially pure enantiomer for the synthesis of 2-methyl-1-(2-thienyl)cyclohexyl piperidine in the form of a substantially pure enantiomer, said synthesis comprising the reaction of 2-methyl-1-(2-thienyl)cyclohexylamine in the form of a substantially pure enantiomer, with a compound of formula Hal-(CH$_2$)$_5$-Hal in which Hal represents a halogen atom, and preferably a chlorine atom, in an inert solvent in the presence of a strong base.

A subject of the invention is also the use of unsaturated compounds of general formula I as defined above, as precursors of molecules labelled with a radioactive tracer such as tritium, obtained by tritiation known to a person skilled in the art.

A subject of the invention is also, as new industrial products, and in particular as new industrial products intended for the preparation of the products of formula (I), the compounds of formula 2 as defined above, in racemic form or in the form of a substantially pure enantiomer.

The following examples are presented in order to illustrate the above procedures and should in no event be considered as a limit to the scope of the invention.

Preparation 1

(±) 1,5-Hexanediol 560 ml of ethyl 4-acetylbutyrate then 2.8 l of toluene are introduced into a 6 l reaction vessel under a nitrogen atmosphere. 980 ml of a 15% by mass solution of lithium tetrahydrogenoaluminate in a toluene/THF mixture, 1/2.4, is placed in the addition funnel. The tetrahydrogenoaluminate is added over 2 hours, allowing the temperature to increase progressively to reflux. The reaction medium is kept under reflux for 3 hours. The reaction vessel is then cooled down to a temperature lower than 15° C., then 110 ml of a 5% soda solution and 250 ml of another 15% soda solution are added very slowly. Agitation is carried out for 15 minutes, then 1 l of methyl tert-butyl ether (MTBE) is added. The reaction medium is agitated for a further 15 minutes, followed by filtering on 270 g of Clarcel and rinsing with 2.8 l of MTBE. All the filtrates are concentrated and 360 g of a quite thick oil is obtained corresponding to the desired product (Yield= 86%).

NMR-$^{13}$C (CDCl$_3$): 21.7; 23.1; 32.1; 38.5; 61.7; 67.3.

Preparation 2

(±) 1,5-Dichlorohexane

Preparation 2a

Starting from Compound 3

352 g of 1,5-hexanediol then 1 l of toluene are introduced into a 3 l three-necked flask under a nitrogen atmosphere. Using a dropping funnel, 660 ml of thionyl chloride is added under vigourous agitation over 2 hours, so as to obtain regular gas evolution and to keep the temperature below 40° C. The reaction medium is then taken progressively to reflux and left under agitation for 1.5 hours. The excess thionyl chloride is then distilled off until the vapour temperature reaches 109° C. A volume of toluene equal to the volume distilled off is then added and a few millilitres are re-distilled, ensuring that the temperature of the vapours is always from 109–110° C. The reaction medium is then cooled down to 20–25° C. and 500 ml of water is added dropwise. Agitation is carried out for 15 minutes then the two phases are decanted. The organic phase is then washed 3 times with 400 ml of a saturated aqueous solution of sodium bicarbonate (pH=7) and with 500 ml of a saturated aqueous solution of sodium chloride. The toluene is eliminated by concentration of the medium, then the oil obtained is distilled under vacuum. After elimination of a 25 g front (Bp$_{3.75}$=39–54° C.), 292 g of an oil corresponding to the desired product is obtained (Bp$_{3.75}$=55–56° C.).

NMR-$^{13}$C (CDCl$_3$): 23.9; 25.2; 31.9; 39.4; 44.6; 58.3.

Preparation 2b

Starting from Compound 7

By proceeding in the same manner as in Preparations 12, 13 and 14 below, and starting from methyl magnesium chloride, the sought compound is obtained. The analytical characteristics are identical to those of the product originating from Preparation 2a.

Preparation 3

Methyl 5-Oxooctanoate 2.82 g of magnesium is introduced into a 250 ml reaction vessel under a nitrogen atmosphere. It is covered with THF and 1 ml of 1-bromopropane is poured in. When the reaction starts, a solution of 9.9 ml of 1-bromopropane in 150 ml of THF is added dropwise over 1.5 hours. Once addition is complete, agitation is carried out for 10 minutes, then the reaction medium is taken to reflux for 3 hours followed by bringing to a temperature of −80° C. A solution of 17 ml of methyl 4-(chloroformyl)butyrate is added very slowly over 45 minutes. Agitation is then carried out for 1 hour at −70° C., then the reaction medium is allowed to return very slowly to 18° C. (over 17 hours). The reaction medium is treated by adding 160 ml of a saturated aqueous solution of ammonium chloride. Agitation is carried out for 30 minutes followed by decanting and re-extraction of the aqueous phase with 100 ml of ether. The organic phases are concentrated. The residue is taken up in 200 ml of ether, then washed twice with 100 ml of water followed by drying over magnesium sulphate and concentration with a rotary evaporator. In this way, 20.2 g of an oil corresponding to the expected product is obtained.

NMR-$^{13}$C (CDCl$_3$): 13.5; 17.1; 18.7; 32.8; 41.2; 44.5; 51.3; 173.4; 210.1.

Preparation 4

Methyl 5-Oxoheptanoate

By operating as in Preparation 3, and starting from 4.5 ml of bromoethane, 9.2 g of the desired product is obtained.

NMR-$^{13}$C (CDCl$_3$): 7.6; 18.8; 32.9; 35.7; 40.9; 51.3; 173.4; 210.5.

Preparation 5

(±) 1,5-Heptanediol

By operating as in Preparation 1, and starting from 5.4 g of methyl 5-oxoheptanoate, 4.2 g of the desired product is obtained.

NMR-$^{13}$C (CDCl$_3$): 9.9; 21.7; 30.0; 32.3; 36.2; 62.0; 72.8.

Preparation 6

(±) 1,5-Octanediol

By operating as in Preparation 1, and starting from 20.0 g of methyl 5-oxooctanoate, 16.9 g of the desired product is obtained.

NMR-$^{13}$C (CDCl$_3$): 14.0; 18.8; 21.7; 32.3; 36.7; 39.5; 62.0; 71.1.

Preparation 7

(±) 1,5-Dichloroheptane 20 ml of DMF is introduced into a 100 ml reaction vessel under a nitrogen atmosphere then cooled down to 0° C. 5.6 ml of thionyl chloride is then added over 10 minutes. Agitation is carried out for 25 minutes, then a solution of 4.2 g of 1,5-heptanediol in 8 ml of DMF is added over 1.5 hours. Agitation is carried out for 1 hour, then the temperature is allowed to return to 20–25° C. The reaction medium is then heated at 95° C. for 45 minutes followed by cooling down to 25° C. 200 ml of water is added followed by extraction three times with 80 ml of diethyl ether. The organic phases are washed twice with 80 ml of water, then dried over potassium carbonate, followed by filtering and concentration with a rotary evaporator. 5.0 g of the desired product is obtained.

NMR-$^{13}$C (CDCl$_3$): 10.9; 23.9; 31.4; 32.1; 37.2; 44.7; 65.2.

Preparation 8

(±) 1,5-Dichlorooctane

By operating as in Preparation 7, and starting from 16.5 g of 1,5-octanediol, 11.8 g of the desired product is obtained.

NMR-$^{13}$C (CDCl$_3$): 13.5; 19.6; 23.8; 32.1; 37.7; 40.5; 44.7; 63.4.

Preparation 9

Pent-2-yn-1,5-diol 26 ml of but-3-yn-1-ol, 55 ml of 30% formaldehyde, 0.41 g of calcium carbonate and finally 4.9 g of cuprous hydroxide prepared just before use by the standard method are introduced successively into a 250 ml three-necked flask. Agitation is carried out for 10 minutes at 20–25° C., then for 96 hours at 80° C., followed by cooling down to 20–25° C. The solution obtained is filtered and concentrated. After distilling under vacuum, 15.3 g of the sought product is obtained (Bp$_{0.05}$=107–109° C.).

NMR-$^{13}$C (CDCl$_3$): 22.8; 50.6; 60.6; 79.9; 83.0.

Preparation 10 cis Pent-2-en-1,5-diol 15.1 g of pent-2-yn-1,5-diol is dissolved in 150 ml of ethyl acetate in a 250 ml three-necked flask. 0.65 ml of chloroform is then added followed by 0.71 g of palladium on barium sulphate (5%). Agitation is carried out for 5 minutes, then the assembly is purged with hydrogen and one equivalent of hydrogen is allowed to be absorbed over 6 and a half hours at 20–25° C. The reaction medium is filtered on celite, followed by rinsing with 50 ml of ethyl acetate and concentration. In this way, 16.4 g of an oil corresponding to the sought product is obtained.

NMR-$^1$H (CDCl$_3$): 2.35 (m, 2H); 3.61 (t, 2H, CH$_2$); 4.1 (d, 2H, CH$_2$); 4.15 (s, 2H, OH); 5.7 (m, 2H, CH=CH).

Preparation 11 cis 1,5-Dibromo pent-2-ene 11 ml of tribromophosphine is introduced into a 100 ml three-necked flask then cooled down to 0° C. 16.4 g of cis pent-2-en-1,5-diol is added over three hours. The temperature is allowed to return slowly to 20–25° C. and agitation is carried out for 15 hours. The reaction medium is then cooled down to 0° C., and 30 ml of water is added over 30 minutes. Agitation is carried out for 5 minutes followed by extraction twice with 30 ml of dichloromethane. The organic phase is washed with 15 ml of water, then dried over magnesium sulphate, filtered and concentrated. In this way, 35 g of an oil is obtained which corresponds to the expected product with sufficient purity to be used in the subsequent stages.

NMR-$^1$H (CDCl$_3$): 2.55 (m, 2H, CH$_2$); 3.43 (t, 2H, CH$_2$Br); 3.97 (d, 2H, BrCH$_2$C=C); 5.88 (m, 2H, CH=CH).

Preparation 12

6-Chloro-1-phenyl-hexan-2-one 10 g of 5-chlorovaleroyl chloride in 50 ml of anhydrous THF is loaded into a 250 ml three-necked flask, under a nitrogen atmosphere. The reaction medium is cooled down to −20° C. and 1.06 g of copper (I) chloride is added. Agitation is carried out for 40 minutes, then 36 ml of a 2 M solution of benzylmagnesium chloride in THF is added over 1.5 hour. Agitation is carried out for 1 hour at −20° C., then the temperature is allowed to return to 20° C. over 1.5 hour. The reaction medium is cooled down to −10° C. and 90 ml of 0.4 M hydrochloric acid is added. Agitation is carried out for 20 minutes, then the aqueous phase is extracted twice with 100 ml of MTBE. The organic phase is washed twice with 50 ml of water, dried over magnesium sulphate, filtered and concentrated. In this way, 13.5 g of sought product is obtained.

Preparation 13

(±) 6-Chloro-1-phenyl-hexan-2-ol 13.1 g of 6-chloro-1-phenyl-hexan-2-one in 75 ml of ethanol is loaded into a 250 ml three-necked flask. The reaction medium is cooled down to −5° C. and a solution of sodium borohydride (2.18 g) in 15 ml of water is added over 5 minutes. Agitation is carried out for 2.5 hours at −5° C., the temperature is allowed to rise to 20° C. over 1 hour, followed by cooling down to −5° C. 110 ml of 0.14 M hydrochloric acid is then added. Agitation is carried out for 10 minutes, followed by extraction 3 times with 80 ml of methylene chloride, drying over magnesium sulphate, filtering and concentration. In this way, 12.3 g of expected product is obtained.

Preparation 14

(±) 2,6-Dichloro-1-phenylhexane

By operating as in Preparation 7 and starting from 12.3 g of 6-chloro-1-phenyl-hexan-2-ol and 12.9 g of thionyl chloride, 13.3 g of expected product is recovered.

Preparation 15

(±) 1,5-Dichloro-1-phenylpentane

By operating as in Preparations 12, 13 and 14 but using phenylmagnesium chloride instead of benzylmagnesium chloride, the sought product is obtained.

Preparation 16

(±) 5-Hexen-2-ol 10 g of 5-hexenone diluted in 20 ml of anhydrous ethyl ether is added dropwise at ambient temperature into a 250 ml two-necked flask placed under argon, containing 2 g of LiAlH$_4$ and 130 ml of anhydrous ethyl ether. The mixture is next taken to reflux for 2 hours. The reaction medium is allowed to return to ambient temperature then cooled in an ice bath. 10 ml of ethanol is added dropwise followed by 20 ml of distilled water. Agitation is stopped in order to allow the white solid formed to deposit, then the supernatant is transferred into a separating funnel. The phases are separated: the aqueous phase is extracted once with ether (5 ml) and the combined ethereal phases are washed with distilled water, dried over MgSO$_4$ and concentrated. 9.5 g of product is obtained in the form of a light oil.

NMR-$^1$H (CDCl$_3$, δ ppm): 1.0 (d, CH$_3$); 1.4 (m, CH$_2$C=C); 2.0 (m, CH$_2$C—O); 3.1 (s, OH); 3.6 (m, CH—O); 4.9 (m, CH$_2$=C); 5.7 (m, CH=C).

NMR-$^{13}$C (CDCl$_3$, δ ppm): 23.0 (CH$_3$); 29.9 (CH$_2$C=C); 38.0 (CH$_2$C—O); 67.0 (CH—O); 114.3 (CH$_2$=C); 138.3 (m, CH=C).

Preparation 17

Δ$^5$-2-Hexenyl Phthalate 8 g (80 mmoles) of 5-hexen-2-ol, 12.1 g (80 mmoles) of phthalic anhydride and 40 ml of pyridine are loaded into a 100 ml single-necked flask. The mixture is agitated at ambient temperature for 4 days. It is next placed in a 500 ml beaker ⅓ filled with crushed ice then acidified with ice cold concentrated HCl. The solution obtained in this way is extracted twice with ice cold chloroform. The combined chloroformic phases are washed three times with ice cold HCl (2N) and three times with a saturated solution of ice cold NaCl then dried over MgSO$_4$ and concentrated. The concentrate is dissolved in a slight excess of an ice cold solution of Na$_2$CO$_3$ (2N, 40 ml) and this solution is extracted twice with ether. It is then acidified with ice cold HCl (2N) until the appearance of a persistent white turbidity then extracted with chloroform. The organic solution is washed with a saturated solution of ice cold NaCl then dried over MgSO$_4$ and concentrated. 16 g of a light oil is obtained in this way. This oil, diluted in 10 ml of petroleum ether, is placed in a cold room (7° C.) overnight under gentle agitation. A very white phthalate precipitate forms which is filtered and dried in order to produce 14.3 g of residue (yield 72.3%).

Preparation 18

Resolution of Δ$^5$-2-Hexenyl Phthalate

A mixture of 14 g of Δ$^5$-2-hexenyl phthalate, 18 g of anhydrous brucine and 200 ml of acetone is taken to reflux in a 250 ml single-necked flask surmounted by a condenser, until a light solution is obtained. The reaction medium is allowed to cool down to ambient temperature. A brucine salt precipitates which is filtered, dried and recrystallized once from acetone in order to produce a mass of 13.6 g. 100 ml of distilled water is added to this salt dissolved while warm in 700 ml of ethanol and 30 ml of HCl (2N), then the cooled solution is extracted four times with ether. The ethereal phase, washed with HCl (2N) and with water, is dried over MgSO$_4$ and concentrated in order to produce 5.5 of a light oil. The oil is hydrolyzed with 50 ml of a solution of NaOH (2N) in a 100 ml single-necked flask and subjected to steam distillation. 2.2 g of a light oil is obtained characterized as being (+)-5-hexen-2-ol. [α]$_D$=+12.2° (c=2.99; Et$_2$O).

(−)-5-hexen-2-ol is obtained by concentrating the solution of the first filtrate to approximately ⅓ of its volume and cooling it down in an ice bath. The brucine salt thus precipitated is filtered, dried and treated like the previous one in order to produce 2.5 g of product. [α]$_D$=−11.1° ([C]=2.5; Et$_2$O).

NMR-$^1$H (CDCl$_3$, δ ppm): 1.0 (d, CH$_3$); 1.4 (m, CH$_2$C=C); 2.0 (m, CH$_2$C—O); 3.1 (s, OH); 3.6 (m, CH—O); 4.9 (m, CH$_2$=C); 5.7 (m, CH=C).

NMR-$^{13}$C (CDCl$_3$, δ ppm): 23.0 (CH$_3$); 29.9 (CH$_2$C=C); 38.0 (CH$_2$C—O); 67.0 (CH—O); 114.3 (CH$_2$=C); 138.3 (m, CH=C).

Preparation 19

(+)-5-Chloro-1-hexene 2.5 g (25 mmoles) of (−)-5-hexen-2-ol and 10 ml of tetrachloromethane are placed in a 100 ml three-necked flask equipped with a condenser, a thermometer and an addition funnel and a solution of 8 g of triphenylphosphine in 10 ml of dichloromethane is added dropwise. The mixture is agitated overnight at 25° C. then cooled down to ambient temperature and concentrated. Adding pentane (20 ml) precipitates Φ$_3$PO which is filtered and the filtrate is concentrated. The concentrate is diluted in pentane and placed in an ice bath for one hour then filtered again. The filtrate is then passed through a silica gel, eluting with pentane. After concentration, 1.3 g of product is obtained. NMR-$^1$H analysis and the rotatory power value indicate that the product obtained by configuration inversion is in fact (+)-5-chloro-1-hexene.

[α]$_D$=+15.5° (c=2.76; Et$_2$O).

NMR-$^1$H (CDCl$_3$, δ ppm): 1.50 (d, CH$_3$); 1.80 (m, CH$_2$C=C); 2.20 (m, CH$_2$C—Cl); 4.0 (m, CH—Cl); 5.1 (m, CH$_2$=C); 5.7 (m, CH=C).

Preparation 20

(+)-5-Chloro-1-hexenol 1 g of (+)-5-chloro-1-hexene and 10 ml of anhydrous ether are placed in a 50 ml three-necked flask under argon, then the mixture is cooled down in an ice bath. 0.5 ml of BH$_3$:S(CH$_3$)$_2$ (10:10.2 M) is added dropwise followed by agitation for one hour at ambient temperature. The reaction medium is then oxidized at 0–5° C. with 4 ml of NaOH (3N) then 8 ml of H$_2$O$_2$ (30%) and the mixture is agitated for one hour at ambient temperature. It is then decanted and the aqueous phase is extracted three times with ether. The combined organic phases are washed with distilled water, dried over MgSO$_4$ and concentrated in order to obtain 0.7 g (60.8%) of 5-chloro-1-hexanol. [α]$_D$=+14.2° C. (c=2.96; Et$_2$O).

NMR-$^1$H (CDCl$_3$, δ ppm): 1.45 (d, CH$_3$); 1.52 (m, 2CH$_2$); 1.60–1.70 (m, CH$_2$C=Cl); 3.16 (s, OH); 3.57 (t, CH$_2$O); 4.1 (m, CH—Cl).

Preparation 21

(+)-1,5-Dichlorohexane

The operating conditions are identical to those for the synthesis of 5-chloro-1-hexene using 400 mg (2.93 mmoles) of (+)-5-chloro-1-hexenol, 3 ml of dichloromethane, 1 g (3.81 mmoles) of triphenylphosphine and 3 ml of tetrachloromethane. 400 mg (85%) of (+)-1,5-dichlorohexane is finally isolated.

[α]$_D$=+13.56° (c=2.68; Et$_2$O).

NMR-$^1$H (CDCl$_3$, δ ppm): 1.50 (d, CH$_3$); 1.60–1.85 (m, 6H, CH$_2$); 3.53 (t, 2H, CH$_2$—Cl); 4.1 (m, CH—Cl).

EXAMPLE 1

(±) cis 2-Methyl-1-(2-thienyl)cyclohexane Carbonitrile 430 g of potash (85%) in 1.7 l of DMF is loaded into a 6 l reaction vessel. The reaction medium is then cooled down to −20° C. and a solution of 191 g of 2-thienylacetonitrile in 0.7 l of DMF is added while cooling down so that the temperature does not exceed −15° C. Once this first phase is complete, a solution of 250 g of 1,5-dichlorohexane in 0.5 l of DMF is immediately added over 1 hour, allowing the temperature to rise to −5° C. Once these two additions are complete, the cooling bath is removed and the temperature is allowed to rise to 20–25° C. over 40 minutes. Agitation is carried out under these conditions for 4.5 hours, then the DMF is eliminated under vacuum. The medium obtained is taken up in 1.5 l of water and extracted twice with 500 ml of heptane. The organic phase is washed twice with 500 ml of water, dried over magnesium sulphate, filtered and the solution obtained is concentrated. A greenish oil is recovered in this way which, after distillation under vacuum, produces 267 g of a colourless oil corresponding to the desired product (Bp$_{2.1}$=90–100° C.).

NMR-$^{13}$C (CDCl$_3$): 18.0; 23.7; 25.4; 32.0; 41.2; 42.8; 48.1; 120.1; 124.4; 125.1; 126.6; 145.0.

EXAMPLE 2

(±) cis 2-Methyl-1-(2-thienyl)cyclohexane Carboxylic Acid 266 g of cis 2-methyl-1-(2-thienyl)cyclohexane carbonitrile in 1 l of diethylene glycol is introduced into a 4 l reaction vessel. After homogenization for 5 minutes and under vigorous agitation, 2.4 kg of a 60% aqueous solution of potash is added. Agitation is then carried out at 170° C. for 24 hours. The reaction medium is cooled down to 20–250 C., then diluted with 1 l of water, poured into 6.5 l of water and washed twice with 3 l of dichloromethane. Under strong agitation, the reaction medium is acidified by adding 2.5 l of concentrated hydrochloric acid. At a temperature below 30° C., the medium is extracted twice with 3 l of dichloromethane. The organic phase is re-extracted twice with 2 l of soda (the first containing 78 g of 99% soda and the second 2 g). The organic phase is removed. The aqueous phase is acidified by adding 1 l of hydrochloric acid (containing 230 ml of concentrated hydrochloric acid) followed by extraction twice with 2 l of dichloromethane. The organic phase is washed with 2 l of water, treated with black and with magnesium sulphate, filtered and concentrated. The whitish solid obtained is crystallized from 1.65 l of heptane under agitation. After filtration and rinsing with heptane, 178 g of a white solid is collected corresponding to the desired product (m.p.=109° C.).

NMR-$^{13}$C (CDCl$_3$): 16.1; 21.2; 22.1; 29.0; 31.5; 37.4; 52.5; 124.8; 125.4; 126.5; 146.5; 180.9.

EXAMPLE 3

(+) cis 2-Methyl-1-(2-thienyl)cyclohexane Carboxylic Acid 30 g of (±) cis 2-methyl-1-(2-thienyl)cyclohexane carboxylic acid and 43.4 g of quinine are dissolved respectively in 2.1 l of warm acetone. These two solutions are mixed and the temperature is allowed to slowly return to 20–25° C., and agitation is carried out at this temperature for 3 hours. The reaction medium is filtered by rinsing with a little acetone. The solution obtained is then concentrated. The salt obtained is recrystallized from 860 ml of acetone. The acid is released from its salt, isolated by treatment with 10% hydrochloric acid and extraction with dichloromethane. The organic phase obtained is concentrated, after drying over magnesium sulphate and filtration. In this way, 8.8 g of the sought (+) acid is collected (m.p.=109° C.).[α]$_D^{20}$=+70.95 (ethanol 0.8%)

NMR-$^{13}$C (CDCl$_3$): identical to the compound of Example 2.

EXAMPLE 4

(−) cis 2-Methyl-1-(2-thienyl)cyclohexane Carboxylic Acid

The first filtrate obtained in the preparation of Example 3 is concentrated to dryness. The acid is released from its salt, isolated by treatment with 10% hydrochloric acid and extraction with dichloromethane. The organic phase obtained is concentrated. 11.9 g of the released acid and 6.1 g of D (+) α-methyl-benzylamine are dissolved respectively in MTBE under reflux of the solvent. The temperature is allowed to slowly return to 20–25° C., followed by agitation for 3 hours. The reaction medium is filtered by rinsing with a little MTBE. The salt obtained is recrystallized from an MTBE/EtOH mixture 7/3, followed by filtration, and the acid is released as previously. 4.0 g of the sought (−) acid is collected in this way (m.p.: 109° C.). [α]$_D^{20}$=−72.1 (ethanol 0.8%).

This acid (−) can also be prepared by reacting (+)-1,5-dichlorohexane with 2-thienylacetonitrile under the operating conditions of Example 1, then converting the nitrile formed in this way into the acid under the operating conditions of Example 2.

NMR-$^{13}$C (CDCl$_3$): identical to the compound of Example 2.

EXAMPLE 5

Ethyl (±) cis 2-Methyl-1-(2-thienyl)cyclohexane Carboxylate

In a 250 ml reaction vessel, 2.5 g of (±) cis 2-methyl-1-(2-thienyl)cyclohexane carboxylic acid is dissolved in 60 ml of toluene. 3 ml of thionyl chloride is then added over 15 minutes. The reaction medium is allowed to homogenize for 5 minutes, then taken progressively to reflux while checking the gas evolution (1 hour). The reaction medium is agitated under reflux for 2 hours. The excess thionyl chloride is then distilled off until vapours are obtained at 108–110° C., followed by the toluene. 60 ml of ethanol is added and the remainder of the toluene is eliminated by distilling the toluene/ethanol azeotrope until vapours are obtained at 77–78° C. At 20–25° C., a solution of 1.5 g of sodium ethanolate in 50 ml of ethanol is added over 20 minutes. The reaction medium is allowed to homogenize for 5 minutes, then taken to reflux for 15 hours. The ethanol is driven off, followed by taking up in 100 ml of water, and extraction three times with 50 ml of ether. The organic phases are washed with 10 ml of water, dried over magnesium sulphate, filtered and concentrated with a rotary evaporator. In this way, 2.36 g of an oil corresponding to the desired product is obtained.

NMR-$^{13}$C (CDCl$_3$): 12.3; 13.9; 21.8; 22.4; 29.3; 32.1; 38.1; 52.7; 60.5; 123.8; 124.8; 126.2; 147.6; 174.0.

EXAMPLE 6

Ethyl (±) trans 2-Methyl-1-(2-thienyl)cyclohexane Carboxylate

By operating as in Example 1 but starting from 3 g of ethyl 2-thiophene acetate instead of 2-thienylacetonitrile, 1.3 g of sought compound is obtained. It is identified by comparing the structures of the compound obtained by basic hydrolysis with the structures of the compound of Example 2.

EXAMPLE 7

(−) cis 2-Methyl-1-(2-thienyl)cyclohexane Carboxylic Acid 50 ml of phosphate buffer (pH=7), 0.15 ml of a solution of 1 g of ethyl (±) cis 2-methyl-1-(2-thienyl)cyclohexane carboxylate in propan-2-ol and 0.46 mg of Porcine Liver Esterase Crude are introduced successively into a 100 ml three-necked flask. The reaction medium is then vigorously agitated for 72 hours at 40° C. followed by cooling down to 20–25° C., filtering on Sephadex then alkanization by adding 20 ml of 5% soda. Extraction is carried out three times with 100 ml of MTBE. The organic phase is washed with 100 ml of water. The aqueous phases are combined then acidified by adding 26 ml of 5% hydrochloric acid. Extraction is carried out three times with 100 ml of MTBE. All the organic phases are washed with 100 ml of water, dried over magnesium sulphate, filtered and concentrated in order to recover 0.4 g of the sought compound.

NMR-$^{13}$C (CDCl$_3$): identical to the compound of Example 4.

EXAMPLE 8

(+) cis 2-Methyl-1-(2-thienyl)cyclohexane Carboxylic Acid

The first MTBE phase obtained in the preparation of Example 7 is dried over magnesium sulphate, filtered and concentrated. The oil obtained is then taken up with 2 ml of ethylene glycol, followed by homogenization. 4.8 g of 60% aqueous potash is then added. Agitation is carried out for 17 hours at 170° C., followed by cooling down to 20–25° C., then 15 ml of water is added. The reaction medium is washed twice with 10 ml of dichloromethane, then acidified with 5 ml of concentrated hydrochloric acid, followed by extraction twice with 10 ml of dichloromethane. All the organic phases are washed with 10 ml of water, dried over magnesium sulphate, filtered and concentrated in order to recover 0.45 g of the sought compound.

NMR-$^{13}$C (CDCl$_3$): identical to the compound of Example 3.

EXAMPLE 9

(±) cis 2-Methyl-1-(2-thienyl)cyclohexane Carboxamide

In a 2 l reaction vessel under a nitrogen atmosphere, 59 g of cis 2-methyl-1-(2-thienyl) cyclohexane carboxylic acid is dissolved in 600 ml of toluene. 71 ml of thionyl chloride is then added over 15 minutes. After homogenization for 5 minutes, the reaction medium is taken progressively to reflux, checking the gas evolution (4 hours). The excess thionyl chloride is then distilled off until vapours are obtained at 108–110° C. The reaction medium is cooled down under these conditions to 10° C., then ammonia is bubbled through at a quite fast rate, without cooling down. The temperature is allowed to rise to 65° C. then to fall back down to 20–30° C. Once the ammonia has been absorbed, agitation is carried out for 1 hour, then the medium is degassed by nitrogen bubbling and 600 ml of water is added. The two phases are decanted, and the aqueous phase is re-extracted with 300 ml of toluene. All the organic phases are washed twice with 250 ml of water and the medium is concentrated. The brownish solid obtained is crystallized from 360 ml of heptane in order to product 52 g of the sought product (m.p.=100° C.).

NMR-$^{13}$C (CDCl$_3$): 15.8; 20.5; 21.9; 29.0; 30.2; 36.2; 52.4; 124.3; 124.8; 126.9; 148.8; 177.1.

EXAMPLE 10

(±) cis 2-Methyl-1-(2-thienyl)cyclohexylamine

In a 1 l three-necked flask, 60 g of potash is dissolved in 240 ml of water. The reaction medium is cooled down to 0° C. 7 ml of bromine is added in one go. After homogenization for 10 minutes, a solution of 20.5 g of cis 2-methyl-1-(2-thienyl) cyclohexane carboxamide and 0.5 g of tetrabutylammonium hydrogen sulphate in 220 ml of dichloromethane is then added rapidly (7 minutes). After agitation for 1 hour, the two phases are decanted. The organic phase is washed with 100 ml of water and the reaction medium is concentrated in order to isolate the intermediate isocyanate.

In a second 1 l three-necked flask, 71 g of soda (99%) is dissolved in 170 ml of water. The reaction medium is cooled down to 20–25° C. A solution of 23.2 g of the intermediate isocyanate and 0.5 g of tetrabutylammonium hydrogen sulphate in 210 ml of MTBE is added rapidly (4 minutes). The reaction medium is agitated under these conditions for 7 hours, then the two phases are decanted. The aqueous phase is extracted with 170 ml of MTBE. The organic phase is washed with 70 ml of water. The organic phase is extracted twice with 200 ml of acidified water (the first containing 100 ml of 5% hydrochloric acid and the second 1 ml). The aqueous phase is washed with 100 ml of MTBE then alkalinized by adding 170 ml of 5% soda and extracted twice with 200 ml of MTBE. The organic phase is washed with 100 ml of water, dried over magnesium sulphate, filtered and concentrated. In this way, 17.2 g of an oil corresponding to the desired amine is obtained.

NMR-$^{13}$C (CDCl$_3$): 15.9; 22.1; 25.9; 30.2; 41.7; 43.7; 56.9; 121.1; 122.5; 126.5; 157.4.

EXAMPLE 11

(+) cis 2-Methyl-1-(2-thienyl)cyclohexylamine 3.0 g of (±) cis 2-methyl-1-(2-thienyl)cyclohexanamine and 2.3 g of (−) tartaric acid are dissolved in the minimum amount of warm 95% aqueous ethanol. The reaction medium is then agitated for 12 hours at 20–25° C., then filtered by rinsing with a little ethanol and heptane. The crystals obtained are recrystallized four times from ethanol 95. The solid is taken up in water and the amine is released by adding 5% soda. The amine is then extracted with ethyl ether, dried over magnesium sulphate and concentrated. 0.25 g of sought product is obtained in this way. $[\alpha]_D^{20}$=+14.7 (methanol, 2%).

NMR-$^{13}$C (CDCl$_3$): identical to the compound of Example 10.

EXAMPLE 12

(−) cis 2-Methyl-1-(2-thienyl)cyclohexylamine

The different filtrates obtained during the preparation of Example 11 are concentrated. The amine is released according to the same protocol as previously. It is then crystallized using (+) tartaric acid in the minimum amount of warm ethanol 95. The reaction medium is then agitated for 12 hours at 20–25° C., followed by filtering by rinsing with a little ethanol and petroleum ether. The crystals obtained are recrystallized three times from ethanol 95. The solid is taken up in water and the amine is released by adding 5% soda. The amine is then extracted with ethyl ether, dried over magnesium sulphate and concentrated. In this way, 0.31 g of sought product is obtained. $[\alpha]_D^{20}$=−15.5 (methanol, 2%).

NMR-$^{13}$C (CDCl$_3$): identical to the compound of Example 10.

EXAMPLE 13

(±) cis 2-Methyl-1-(2-thienyl)cyclohexyl Piperidine

In a 250 ml three-necked flask, 5.7 g of cis 2-methyl-1-(2-thienyl)cyclohexanamine and 5 ml of 1,5-dibromopentane are dissolved in 60 ml of sulpholane. After homogenization for 5 minutes, 11.7 g of potassium carbonate and 2.1 g of sodium iodide are added in one go. The reaction medium is allowed to homogenize for a further 5 minutes then taken to 80° C. for 20 hours, followed by cooling down to 25–30° C. and treatment by adding 300 ml of water and 100 ml of MTBE. The two phases are decanted. The aqueous phase is re-extracted with 150 ml of MTBE. The organic phase is washed with 100 ml of water. The organic phase is extracted twice with 150 ml of acidified water (the first containing 40 ml of 5% hydrochloric acid and the second 10 ml). The combined acid aqueous phases are washed with 100 ml of MTBE and the organic phases are separated. The aqueous phases are alkalinized by adding 70 ml of 5% soda and extracted twice with 100 ml of MTBE. The extraction organic phase is washed with 50 ml of water, treated with black and magnesium sulphate, filtered on clarcel and concentrated. In this way, 7.5 g of a residue is collected, which is crystallized from 150 ml of methanol. 5.9 g of a white solid is then recovered, corresponding to the sought molecule (m.p.=81–82° C.).

NMR-$^{13}$C (CDCl$_3$): 14.0; 19.4; 23.1; 25.1; 27.0; 29.5; 30.1; 33.9; 46.0; 52.7; 122.1; 124.0; 125.9; 144.7.

EXAMPLE 14

(±) cis 2-Methyl-1-(2-thienyl)cyclohexyl Piperidinium Hydrochloride 57 ml of a 1M solution of hydrochloric acid in MTBE is introduced into a 250 ml three-necked flask. Under vigourous agitation and under a nitrogen atmosphere, a solution of 5 g of (±) cis 2-methyl-1-(2-thienyl)cyclohexyl piperidine in 45 ml of MTBE is added quite quickly. Once the addition is complete, agitation is maintained for 3 hours followed by filtration and drying under 1 torr at 45° C. In this way, 5.4 g of sought product is collected (m.p.=230–1° C.).

NMR-$^{13}$C (CDCl$_3$): 15.8; 17.8; 22.1; 22.3; 22.5; 22.6; 26.5; 30.2; 35.4; 46.7; 48.9; 72.9; 127.2; 127.6; 130.1; 136.9.

EXAMPLE 15

(+) cis 2-Methyl-1-(2-thienyl)cyclohexyl Piperidinium Hydrochloride

15a. Chemical Resolution 17.53 g of (±) cis 2-methyl-1-(2-thienyl)cyclohexyl piperidine and 12.7 g of (−) di-O,O'-toluoyl tartaric acid are dissolved respectively in the minimum amount of warm isopropanol. These two solutions are mixed and then allowed to slowly return to 20–25° C., and then agitated for 4 hours. The reaction medium is filtered by rinsing with a little isopropanol and heptane. The solid is taken up in water and the amine is released by adding 5% soda. The amine is then extracted with MTBE, dried over magnesium sulphate and concentrated. The rate of enrichment in enantiomer (+) is measured by chiral column HPLC and the crystallization operation is repeated three more times, adjusting the quantity of (−) di-O,O'-toluoyltartaric acid to the previous stoichiometric ratio. In this way, 3.2 g of the amine (+) is collected with an enantiomeric excess greater than 99%. The hydrochlorination of the amine is carried out in an identical manner to that described during the preparation of Example 14, and allows 3.6 g of sought product to be obtained (m.p.=230–1° C.).

The NMR is identical to that of the product of Example 14.

15b. Chemical Synthesis

By operating as indicated during the preparation of Examples 9, 10, 13 and 14 and using 23.2 g of (+) cis 2-methyl-1-(2-thienyl)cyclohexane carboxylic acid, 18.2 g of the sought (+) hydrochloride is obtained (m.p.=230–1° C.). $[\alpha]^D_{24}$=+33.0.

The NMR is identical to that of the product of Example 14.

EXAMPLE 16

(−) cis 2-Methyl-1-(2-thienyl)cyclohexyl Piperidinium Hydrochloride

16a. Chemical Resolution

The first filtrate obtained during the preparation of Example 15a. is concentrated, and the crystallization operation is carried out using (+) di-O,O'-toluoyltartaric acid under the same conditions as previously, three times in succession. After hydrochlorination, 3.7 g of the sought compound is isolated (m.p.=230–1° C.).

The NMR is identical to that of the product of Example 14.

16b. Chemical Synthesis

By operating as indicated during the preparation of Examples 9, 10, 13 and 14 and using 11.5 g of (−) cis 2-methyl-1-(2-thienyl)cyclohexane carboxylic acid, 8.1 g of the sought (−) hydrochloride is obtained (m.p.=230–1° C.).

The NMR is identical to that of the product of Example 14.

$[\alpha]^D_{24}$=−32.3

EXAMPLE 17

N-[α-methyl-((S)-phenylmethyl)]cis 2-Methyl-1-(2-thienyl)cyclohexane Carboxamide In a 100 ml reaction vessel under a nitrogen atmosphere, 2.0 g of cis 2-methyl-1-(2-thienyl)cyclohexane carboxylic acid is dissolved in 20 ml of toluene. 1.3 ml of thionyl chloride is then added over 5 minutes. After homogenization for 5 minutes, the reaction medium is taken progressively to reflux, checking the gas evolution (1 hour). The excess thionyl chloride is then distilled off until vapours are obtained at 108–110° C. The reaction medium is cooled down to 20° C., then a solution of 2.55 g of α-methyl-(S)-phenylmethylamine in 40 ml of toluene is added over 15 minutes without cooling down. The temperature is allowed to rise to 40° C. then go back down to 20–30° C. Agitation is carried out at 25° C. for 2 hours, then 40 ml of water is added. The two phases are decanted. The organic phase is washed twice with 40 ml of water, 40 ml of hydrochloric acid and 40 ml of water. After concentration of the reaction medium, the solid residue obtained is crystallized from 40 ml of pentane in order to produce 2.4 g of sought product.

TLC (SiO$_2$ 60F254, eluant hexane/diethyl ether 5/5, UV visualization, Rf=0.66).

EXAMPLE 18

(±) cis 2-Methyl-1-(3-thienyl)cyclohexane Carbonitrile 43 g of potash in 160 ml of DMF is placed in a 500 ml three-necked flask. The reaction medium is cooled down to −10° C. and a solution of 17.6 g of 3-thienylacetonitrile in 40 ml of DMF is added dropwise over 30 minutes while maintaining the temperature at −10° C. Agitation is then carried out for 20 minutes. A solution of 24.7 g of 1,5-dichlorohexane in 40 ml of DMF is then added over 30 minutes at −10° C. Agitation is then carried out for 15 minutes, and the reaction medium is allowed to return to 20–25° C. over 1.5 hours. Agitation is then carried out for 18 hours at 25° C., then for 4 hours at 60° C. The temperature is allowed to return to 20–25° C. after driving off the DMF under vacuum, followed by taking up in 1 l of water. Extraction is carried out using 600 ml then 400 ml of heptane. The organic phase is washed with 400 ml of water then 400 ml of a solution of sodium chloride. The solution obtained is dried over magnesium sulphate, filtered and concentrated. After distillation under vacuum, 15.2 g of a colourless oil is obtained corresponding to the desired product (Bp$_{0.08}$=114–120° C.).

NMR-$^{13}$C (CDCl$_3$): 17.9; 23.5; 25.2; 34.7; 39.1; 40.7; 47.8; 121.2; 121.3; 124.7; 126.6; 142.1.

EXAMPLE 19

(±) cis 2-Methyl-1-(3-thienyl)cyclohexane Carboxylic Acid

Starting from 15.0 g of (±) cis 2-methyl-1-(3-thienyl) cyclohexane carbonitrile and proceeding in the same manner as that described in the preparation of Example 2, 11.6 g of the sought compound is obtained after crystallization from 4 volumes of heptane.

EXAMPLE 20

(±) cis 2-Methyl-1-(3-thienyl)cyclohexane Carboxamide

Starting from 11.6 g of (±) cis 2-methyl-1-(3-thienyl) cyclohexane carboxylic acid and proceeding in the same manner as that described in the preparation of Example 9, 12.0 g of the sought compound is obtained after crystallization from 5 volumes of heptane.

NMR-$^{13}$C (CDCl$_3$): 16.0; 21.2; 22.1; 29.1; 30.8; 35.6; 52.1; 121.4; 126.1; 126.9; 145.1; 177.5.

EXAMPLE 21

(±) cis 2-Methyl-1-(3-thienyl)cyclohexanamine

Starting from 11.6 g of (±) cis 2-methyl-1-(3-thienyl) cyclohexane carboxamide and proceeding in the same manner as that described in the preparation of Example 10, 6.9 g of a practically colourless oil is obtained corresponding to the sought compound.

NMR-$^{13}$C (CDCl$_3$): 15.2; 15.9; 21.9; 26.1; 30.1; 40.3; 41.8; 56.3; 118.9; 125.2; 125.5; 152.4.

EXAMPLE 22

(±) cis 2-Methyl-1-(3-thienyl)cyclohexyl Piperidine

Starting from 5.7 g of (±) cis 2-methyl-1-(3-thienyl) cyclohexanamine and proceeding in the same manner as that described in the preparation of Example 13, 5.9 g of the sought compound is obtained after crystallization from 14 volumes of methanol.

NMR-$^{13}$C (CDCl$_3$): 13.7; 19.6; 23.0; 25.1; 27.0; 28.8; 29.3; 32.7; 46.0; 62.2; 120.8; 123.1; 127.8; 141.1.

EXAMPLE 23

(±) cis 2-Methyl-1-(3-thienyl)cyclohexyl Piperidinium Hydrochloride

Starting from 0.7 g of (±) cis 2-methyl-1-(3-thienyl) cyclohexyl piperidine and proceeding in the same manner as that described in the preparation of Example 14, 0.62 g of the sought hydrochloride is obtained (m.p.=230° C.).

NMR-$^{13}$C (CDCl$_3$): 15.5; 18.1; 22.1; 22.3; 22.6; 25.8; 29.9; 33.5; 46.6; 48.8; 72.0; 126.5; 126.6; 134.2.

EXAMPLE 24

(±) [cis 2-Methyl-1-(2-thienyl)cyclohexyl]1,2,3,6-tetrahydropyridine

Starting from 11.51 g of (±) cis 2-methyl-1-(2-thienyl) cyclohexanamine and 35 g of cis-1,5-dibromo pent-2-ene and proceeding in the same manner as that described in the preparation of Example 13, 15.2 g of a beige solid is obtained which is purified by chromatography on 590 g of alumina (Merck 90) (Eluant heptane). In this way, 4.81 g of sought compound is obtained.

NMR-$^{13}$C (CDCl$_3$): 14.1; 19.4; 23.0; 27.3; 29.4; 29.9; 34.4; 42.1; 44.5; 62.9; 122.6; 124.5; 124.8; 126.0; 126.5; 143.6.

EXAMPLE 25

(±) [cis 2-Methyl-1-(2-thienyl)cyclohexyl]1,2,3,6-tetrahydropyridinium Hydrochloride Starting from 0.24 g of (±) [cis 2-methyl-1-(2-thienyl) cyclohexyl]1,2,3,6-tetrahydropyridine and proceeding in the same manner as that described in the preparation of Example 14, 0.2 g of the sought compound is recovered (m.p.= 182–184° C.).

EXAMPLE 26

(±) cis 2-Ethyl-1-(2-thienyl)cyclohexane Carbonitrile

By operating in the same manner as for the preparation of Example 1 but starting from 4.8 g of 1,5-dichloroheptane instead of 1,5-dichlorohexane, 2.8 g of the desired product is obtained.

NMR-$^{13}$C (CDCl$_3$): 10.1; 22.3; 23.1; 23.9; 26.8; 41.4; 46.9; 47.9; 118.9; 123.0; 123.7; 125.0; 143.8.

EXAMPLE 27

(±) cis 2-Propyl-1-(2-thienyl)cyclohexane Carbonitrile

By operating in the same manner as in Example 1 but starting from 5.1 g of 1,5-dichlorooctane instead of 1,5-dichlorohexane, 3.3 g of the desired product is obtained.

NMR-$^{13}$C (CDCl$_3$): 13.9; 23.8; 24.9; 25.4; 28.9; 33.9; 42.0; 47.1; 47.8; 120.5; 124.4; 125.2; 126.4; 145.3.

EXAMPLE 28

(±) cis 2-Benzyl-1-(2-thienyl)cyclohexane Carbonitrile

By operating in the same manner as in Example 1 but using 2,6-dichloro-1-phenylhexane instead of 1,5-dichlorohexane, the sought product is obtained.

EXAMPLE 29

(±) cis 2-Phenyl-1-(2-thienyl)cyclohexane Carbonitrile

By operating in the same manner as in Example 1 but using 1,5-dichloro-1-phenylpentane instead of 1,5-dichlorohexane, the sought product is obtained.

Using the process indicated above, the following products can also be prepared, which are also part of the invention and which constitute preferred products:

TABLE 1

| Compound | R | R' | R" |
|---|---|---|---|
| A | CO$_2$H | 2-thienyl | propyl |
| B | CO$_2$Et | 2-thienyl | propyl |
| C | C(O)NH$_2$ | 2-thienyl | propyl |
| D | NH$_2$ | 2-thienyl | propyl |
| E | CO$_2$H | 2-thienyl | benzyl |
| F | CO$_2$Et | 2-thienyl | benzyl |
| G | C(O)NH$_2$ | 2-thienyl | benzyl |
| H | NH$_2$ | 2-thienyl | benzyl |
| I | NHMe | 2-thienyl | phenyl |
| J | C(O)NHMe | 2-thienyl | 3-chlorophenyl |
| K | NH$_2$ | 2-thienyl | phenyl |
| L | CO$_2$H | 2-thienyl | cyclohexyl |
| M | C...N | 3-thienyl | butyl |
| N | CO$_2$H | 3-thienyl | propyl |
| O | C(O)NH$_2$ | 3-thienyl | propyl |
| P | C...N | 2-thienyl | allyl |
| Q | C...N | 2-thienyl | 3-trifluromethyl phenyl |
| R | NHC$_3$H$_7$ | 3-thienyl | methoxyphenyl |
| S | C...N | 3-thienyl | benzyl |

TABLE 1-continued

| Compound | R | R' | R" |
|---|---|---|---|
| T | C...N | 3-thienyl | methoxymethyl |
| U | CO$_2$Me | 2-thienyl | cyclohexyl |
| V | CO$_2$Et | 2-thienyl | benzyl |
| W | CO$_2$Et | 2-thienyl | phenethyl |
| X | hydroxymethyl | 3-thienyl | allyl |
| Y | CO$_2$Me | 3-thienyl | 3,4-dichlorophenyl |

What is claimed is:

1. A process for the preparation of cyclic (thienylcyclohexyl) amines comprising reacting a compound of claim 1 wherein R" is alkyl with a compound of the formula Hal-(CH$_2$)$_5$-Hal wherein Hal is hydrogen.

2. The process of claim 1 wherein Hal is chlorine.

3. The process of claim 1 wherein the compound of claim 1 is in the form of a substantially pure enantiomer.

4. The process of claim 1 wherein the reaction is effected in the presence of a strong base.

5. A compound selected from the group consisting of diastereoisomer, enantiomer or racemate of a compound of the formula

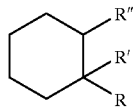   I wherein R is selected from the group consisting of —CN,

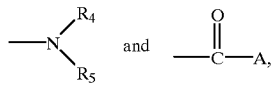

A is selected from the group consisting of halogen, —OR$_1$, and

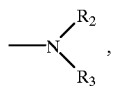

R$_1$, R$_2$ and R$_3$ are independently selected from the group consisting of hydrogen and unsubstituted or substituted alkyl, alkenyl and alkynyl of up to 6 carbon atoms, the substituents being at least one member of the group consisting of halogen, hydroxy, alkoxy and alkylthio of 1 to 6 carbon atoms, acyl of an organic carboxylic acid of 1 to 6 carbon atoms, carboxy, salified carboxy, carboxy esterified with an alkanol of 1 to 6 carbon atoms, —CN, —NO$_2$, —NH$_2$, mono and dialkylamino of 1 to 6 alkyl carbon atoms and unsubstituted or substituted cycloalkyl of 3 to 7 carbon atoms and hydrocarbonyl aryl, the said substituents being at least one member of the group consisting of halogen, —OH, acyl of an organic carboxylic acid of 1 to 6 carbon atoms, carboxy, salified carboxy, carboxy esterified with alkanol of 1 to 6 carbon atoms, —CN, —NO$_2$, —NH$_2$, mono and dialkylamino of 1 to 6 alkyl carbon atoms and alkyl, alkenyl, haloalkyl, alkoxy and alkylthio of up to 6 carbon atoms, R$_4$ and R$_5$ are individually selected from the group consisting of unsubstituted or substituted alkyl, alkenyl and alkynyl of up to 6 carbon atoms, the substituents being at least one member of the group consisting of halogen, hydroxy, alkoxy and alkylthio of 1 to 6 carbon atoms, acyl of an organic carboxylic acid of 1 to 6 carbon atoms, carboxy, salified carboxy, carboxy esterified with an alkanol of 1 to 6 carbon atoms, —CN, —NO$_2$, —NH$_2$, mono and dialkylamino of 1 to 6 alkyl carbon atoms and unsubstituted or substituted cycloalkoxy of 3 to 7 carbon atoms and hydrocarbonyl aryl, the said substituents being at least one member of the group consisting of halogen, —OH, acyl of an organic carboxylic acid of 1 to 6 carbon atoms, carboxy, salified carboxy, carboxy esterified with alkanol of 1 to 6 carbon atoms, —CN, —NO$_2$, —NH$_2$, mono and dialkylamino of 1 to 6 alkyl carbon atoms and alkyl, alkenyl, haloalkyl, alkoxy and alkylthio of up to 6 carbon atoms, R' is 2-thienyl or 3-thienyl, R" is selected from the group consisting of a) unsubstituted or substituted alkyl, alkenyl and alkynyl of up to 6 carbon atoms, the substituents being at least one member of the group consisting of halogen, —OH, alkyl and alkylthio of 1 to 6 carbon atoms, acyl of an organic carboxylic acid of 1 to 6 carbon atoms, carboxy, salified carboxy, carboxy esterified with an alkanol of 1 to 6 carbon atoms, —CN, —NO$_2$, —NH$_2$, mono and dialkylamino of 1 to 6 alkyl carbon atoms and unsubstituted and substituted cycloalkyl of 3 to 7 carbon atoms and unsubstituted and substituted carbocyclic aryl, the substituents being at least one member of the group consisting of halogen, alkoxy and alkylthio of 1 to 6 carbon atoms, —OH, alkenyl of up to 6 carbon atoms, acyl of an organic carboxylic acid of 1 to 6 carbon atoms, carboxy, salified carboxy, carboxy esterified with alkanol of 1 to 6 carbon atoms, alkyl of 1 to 6 carbon atoms, —CN, —NO$_2$, —NH$_2$ and mono and dialkylamino of 1 to 6 alkyl carbon atoms, b) unsubstituted or substituted cycloalkyl and cycloalkenyl of 3 to 7 carbon atoms, the substituents being at least one member of the group consisting of halogen, —OH, acyl of an organic carboxylic acid of 1 to 6 carbon atoms, carboxy, salified carboxy, carboxy esterified with alkanol of 1 to 6 carbon atoms, —CN, —NO$_2$, —NH$_2$, mono and dialkylamino of 1 to 6 alkyl carbon atoms and alkyl, alkenyl, haloalkyl, alkoxy and alkylthio of up to 6 carbon atoms, c) unsubstituted or substituted hydrocarbonyl aryl, the substituents being at least one member of the group consisting of halogen, —OH, acyl of an organic carboxylic acid of 1 to 6 carbon atoms, carboxy, salified carboxy, carboxy esterified with alkanol of 1 to 6 carbon atoms, —CN, —NO$_2$, —NH$_2$, mono and dialkylamino of 1 to 6 carbon atoms and alkyl, alkenyl, haloalkyl, alkoxy and alkylthio of up to 6 carbon atoms and their non-toxic, pharmaceutically acceptable acid addition salts with the proviso that when R is amino and R' is 2-thienyl, R" is not methyl.

6. A compound of claim 5 wherein R is selected from the group consisting of —CN,

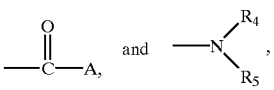

A is selected from the group consisting of chlorine, —OR$_1$ and

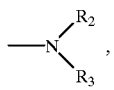

$R_1$, $R_2$ and $R_3$ are individually selected from the group consisting of hydrogen and unsubstituted or substituted alkyl, alkenyl and alkynyl of up to 6 carbon atoms, the substituents being at least one member of the group consisting of fluorine, chlorine, bromine, iodine, hydroxy, methoxy, ethoxy, isopropyloxy, ter-butyloxy, methylthio, ethylthio, propylthio, butylthio, pentylthio, acyl, carboxy, cyano, nitro, amino, mono and dialkylamino, cyclopropyl, cyclobutyl, cyclopentyl, cyclohexyl, cycloheptyl and phenyl, the cyclopropyl, cyclobutyl, cyclopentyl, cyclohexyl, cycloheptyl and phenyl being optionally substituted, $R_4$ and $R_5$ are individually selected from the group consisting of hydrogen and unsubstituted and substituted alkyl, alkenyl and alkynyl of up to 6 carbon atoms, the substituent being at least one member of the group consisting of a) fluorine, chlorine, bromine, iodine, hydroxy, methoxy, ethoxy, isopropyloxy, ter-butyloxy, methylthio, ethylthio, propylthio, butylthio, pentylthio, acyl, carboxy, cyano, nitro, amino, mono and dialkylamino, cyclopropyl, cyclobutyl, cyclopentyl, cyclohexyl, cycloheptyl and phenyl, the cyclopropyl, cyclobutyl, cyclopentyl, cyclohexyl, cycloheptyl and phenyl being optionally substituted, R' is 2-thienyl or 3-thienyl, R" is selected from the group consisting of a) unsubstituted or substituted alkyl, alkenyl and alkynyl of up to 6 carbon atoms, the substituents being at least one member of the group consisting of fluorine, chlorine, bromine or iodine atoms, hydroxy, methoxy, ethoxy, isopropyloxy, ter-butyloxy, methylthio, ethylthio, propylthio, butylthio, pentylthio, acyl, carboxy, cyano, nitro, amino, mono and dialkylamino, cyclopropyl, cyclobutyl, cyclopentyl, cyclohexyl, cycloheptyl and phenyl, the cyclopropyl, cyclobutyl, cyclopentyl, cyclohexyl, cycloheptyl and phenyl being optionally substituted b) unsubstituted or substituted cyclopropyl, cyclobutyl, cyclopentyl, cyclohexyl and cycloheptyl, the substituents being at least one member of the group consisting of fluorine, chlorine, bromine, iodine, hydroxy, methoxy, ethoxy, isopropyloxy, ter-butyloxy, methylthio, ethylthio, propylthio, butylthio, pentylthio, acyl, carboxy, cyano, nitro, mono and dialkylamino and c) unsubstituted or substituted phenyl and naphthyl, the substituents being at least one member of the group consisting of fluorine, chlorine, bromine, iodine, hydroxy, methoxy, ethoxy, isopropyloxy, ter-butyloxy, methylthio, ethylthio, propylthio, butylthio, pentylthio, acyl, carboxy, cyano, nitro, mono and dialkylamino.

7. A compound of claim 5 selected from the group consisting of
2-methyl-1-(2-thienyl)cyclohexane carbonitrile,
2-methyl-1-(2-thienyl)cyclohexane carboxylic acid,
ethyl 2-methyl-1-(2-thienyl)cyclohexane carboxylate,
2-methyl-1-(2-thienyl)cyclohexane carboxamide,
N-[α-methyl-((S)-benzyl)]2-methyl-1-(2-thienyl) cyclohexane carboxamide,
2-methyl-1-(3-thienyl)cyclohexane carbonitrile,
2-methyl-1-(3-thienyl)cyclohexane carboxylic acid,
2-methyl-1-(3-thienyl)cyclohexane carboxamide,
2-methyl-1-(3-thienyl)cyclohexylamine,
2-ethyl-1-(2-thienyl)cyclohexane carbonitrile,
2-propyl-1-(2-thienyl)cyclohexane carbonitrile,
2-benzyl-1-(2-thienyl)cyclohexane carbonitrile and
2-phenyl-1-(2-thienyl)cyclohexane carbonitrile.

8. A process for the preparation of a compound of claim 5 wherein R is —CN or

comprising reacting a compound of the formula

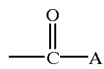

wherein R and R' are defined as in claim 5 with a compound of the formula

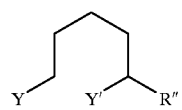

wherein R" is as defined in claim 5 and Y and Y' are leaving groups.

* * * * *

UNITED STATES PATENT AND TRADEMARK OFFICE
CERTIFICATE OF CORRECTION

PATENT NO. : 6,107,495
DATED : August 22, 2000
INVENTOR(S) : Cazaux et al.

It is certified that error appears in the above-identified patent and that said Letters Patent is hereby corrected as shown below:

<u>Column 23,</u>
Line 15, change "1" to -- 5 --.

Signed and Sealed this

Eighth Day of October, 2002

*Attest:*

*Attesting Officer*

JAMES E. ROGAN
*Director of the United States Patent and Trademark Office*